(12) United States Patent
Vallejo et al.

(10) Patent No.: US 7,507,373 B2
(45) Date of Patent: Mar. 24, 2009

(54) ASSAY DEVICE FOR THE TESTING OF FLUID SAMPLES

(75) Inventors: Yli Remo Vallejo, Newark, DE (US); Martin Gould, Mullica Hill, NJ (US)

(73) Assignee: American Bio Medica Corp., Kinderhook, NY (US)

( * ) Notice: Subject to any disclaimer, the term of this patent is extended or adjusted under 35 U.S.C. 154(b) by 426 days.

(21) Appl. No.: 11/007,251

(22) Filed: Dec. 9, 2004

(65) Prior Publication Data

US 2006/0127274 A1    Jun. 15, 2006

(51) Int. Cl.
*G01N 33/00* (2006.01)

(52) U.S. Cl. ............................. 422/56; 422/50; 422/55; 422/58; 422/68.1; 422/82.09; 422/99; 422/100; 422/102

(58) Field of Classification Search ............. 422/50, 422/55, 56, 58, 68.1, 82.09, 99, 100, 102
See application file for complete search history.

(56) References Cited

U.S. PATENT DOCUMENTS 6,548,019 B1 * 4/2003 Lee et al. ................. 422/58

* cited by examiner

*Primary Examiner*—Sam P Siefke
(74) *Attorney, Agent, or Firm*—Edmund M. Jaskiewicz

(57) ABSTRACT

An assay device for testing of liquid samples for drugs of abuse has a transparent container for retaining a liquid sample. A backing member is within the container and is curved so that its front surface corresponds to the curvature of the container wall. Immunoassay test strips are on the front face of the backing and are visible through the container wall. Each test strip is enclosed in a transparent pocket which has a bottom opening through which the bottom portion of the test strip protrudes to contact the liquid sample within the container. The liquid then flows upwardly through the test strip to react with reagents within the test strip.

3 Claims, 4 Drawing Sheets

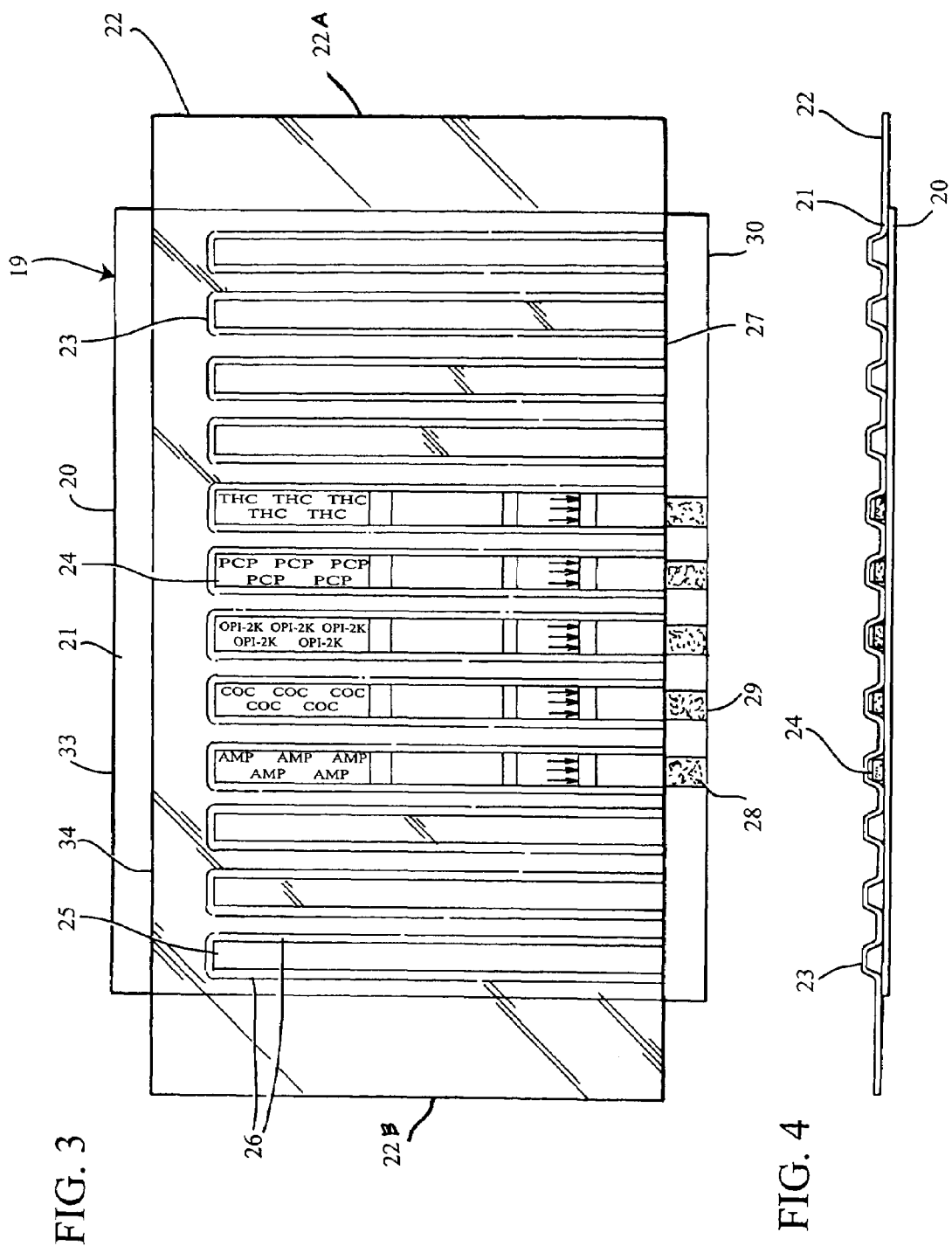

ASSAY DEVICE FOR THE TESTING OF FLUID SAMPLES

FIELD OF THE INVENTION

The present invention relates to assay devices for the testing of liquid samples for determining the presence of undesirable chemical constituents, more particularly, to a test device having a container for retaining a liquid sample and test strips within the container for indicating visually the presence of particular drugs of abuse.

BACKGROUND ART

The increased availability and use of drugs of abuse by the general population has caused employers, governmental agencies, sports groups and other organizations to utilize drug screening both as a condition of employment and in order to maintain safety in the work-place. Typical drug screening tests are performed for the purpose of quickly identifying on a qualitative basis the presence of drugs in a body fluid which may be urine. A complete analysis of the sample might then be carried out in a laboratory in the event that the preliminary screening results are positive. More and more such drug screenings are taking place on site or the workplace and are generally carried out by testing personnel who may have only limited technical training. It is thus important that the drug screening procedure is simple to perform but yield reliable results. Further, the test device must be such so as to enable the testing personnel to avoid any contact with the fluid specimen which is being tested.

Various forms of devices which have been proposed for the collection and taking of body fluids, such as urine, have proved to be cumbersome in operation since they involve a number of separate steps. Initially, the sample was collected and several additional steps were then required to transfer the urine sample to an analysis device. This multiple step procedure required the manual handling of the specimen through various devices and the use of such transfer devices inevitably caused spills which may result in contamination to the tester and surroundings. In addition, non technical personnel who perform the screening tests on urine samples objected to coming into any kind of contact with the urine sample and even the handling of the sample itself.

Another form of a testing device required the transfer of the specimen or at least a portion thereof, to another compartment of the collection container in order to perform the test This transfer of the specimen required vigorous shaking of the container or turning the container upside down in order to cause the flow of the specimen into a test compartment. It was therefore necessary to make the containers leak proof under such conditions and the result was a complicated and expensive container structure.

The testing device also included a screen test card for drugs of abuse which comprised a thin flat member having a plurality of immunoassay test strips fastened side by side in parallel on at least one side of the test card. Each test strip is reactive to provide a visual indication in response to a particular drug of abuse.

The test card was insertable into a cup-like container so as to have one end immersed in a urine sample retained in the container to a predetermined depth whereby the visual results of each test strip could be seen through a transparent wall of the container or above the container without removing the test card from the container. The test card thus provides for the simultaneous detection of multiple analytes. If the sample should test "positive" to indicate the presence of a drug in the urine, it is necessary to send the sample to a certified laboratory for confirmatory testing.

Another form of a prior art assay device is disclosed in U.S. Pat. Nos. 6,379,620 and 6,497,843. This form of assay device includes a container for a liquid sample and an assay assembly within the container. The assay assembly has test or assay strips mounted to contact a wicking material which contacts the liquid sample and serves as a path for the liquid sample to react with chemical agents on the strips to give positive, negative or inclusive results.

However, such an assay device requires a precise relationship between the several components of the assay assembly in order that the assay device functions in the manner intended. This necessary relationship was difficult to obtain during the manufacture of the components of the assay assembly and their subsequent assembly within the container.

BRIEF SUMMARY OF THE INVENTION

It is therefore the principal object of the present invention to provide a novel and improved assay device and process for testing of liquid samples for drugs of abuse.

It is another object of the present invention to provide such an assay device having a novel and improved arrangement of the assay or test elements within a container for retaining a liquid sample.

It is an additional object of the present invention to provide a simple and effective assembly of test elements within a container for retaining a liquid sample.

It is a further object of the present invention to provide such an assay device which facilitates the drug screening procedure.

The objects of the present invention are achieved and the disadvantages of the prior art are eliminated by the assay test device according to the present invention which may comprise a transparent container for retaining a liquid sample to be tested and one or more immunoassay test strips mounted vertically on the front surface of a liquid impermeable backing member within the container such that the strips are visible through the wall of the container. The top and side edges of each test strip are enclosed and sealed by a retaining or cover member so as to expose a bottom portion of each test strip to contact the liquid sample which flows upwardly into the test strip to react with chemical agents within this strip to indicate the presence or absence of particular drugs of abuse. The cover member is preferably transparent so that the test results on the test strips are viewable.

The container is preferably a cup-like member having a cylindrical side wall which may be tapering and an open top end which is closed by a detachable cover or cap. The backing member is flexible and when assembled within conforms to the inner curvature of the cylindrical wall. The backing member may extend around a major portion of the periphery of the container and has a height substantially equal to the inner height of the container.

The cover member may comprise a single flexible sheet-like element having a plurality of pockets formed therein to accommodate the test strips and is attached to the front surface of the backing member.

The process for testing of liquid samples for drugs of abuse according to the present invention, comprises introducing a liquid sample into a transparent container having an assay assembly therein for chemically analyzing a urine sample. The assay assembly has a backing member and one or more immunoassay test strips are disposed axially on the front surface of the backing member so as to be visible through the container wall. Each of the test strips is enclosed and sealed along its sides and top edge by a transparent cover such that a bottom portion of each test strip is exposed to contact the liquid sample within the container. The liquid sample is then allowed to wick up the test strips by capillary action. The test results are then read on each test strip through the wall of the transparent container.

BRIEF DESCRIPTION OF THE SEVERAL VIEWS OF THE DRAWINGS

Other objects and advantages of the present invention will be apparent upon reference to the accompanying description when taken in conjunction with the following drawings, which are exemplary wherein;

FIG. 3 is a plan view of the assay assembly in a flattened position;

FIG. 4 is an elevational view of the assay assembly shown in FIG. 3 from an end thereof;

DETAILED DESCRIPTION OF THE INVENTION

Figure 1:
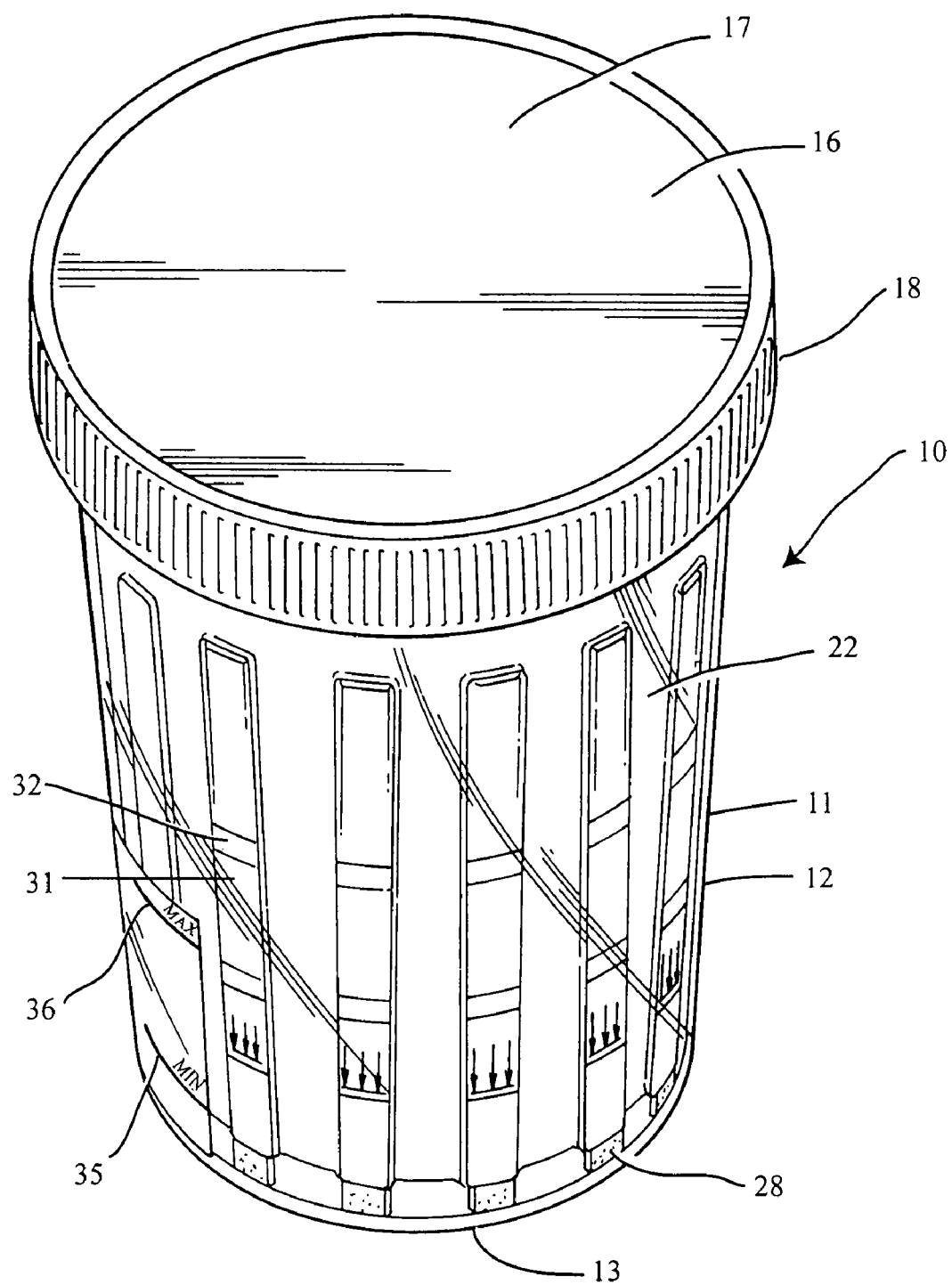
FIG. 1 is a perspective view of the assay device according to the present invention generally showing the container closed by a cover, and the test strips mounted in the container.
Figure 2:
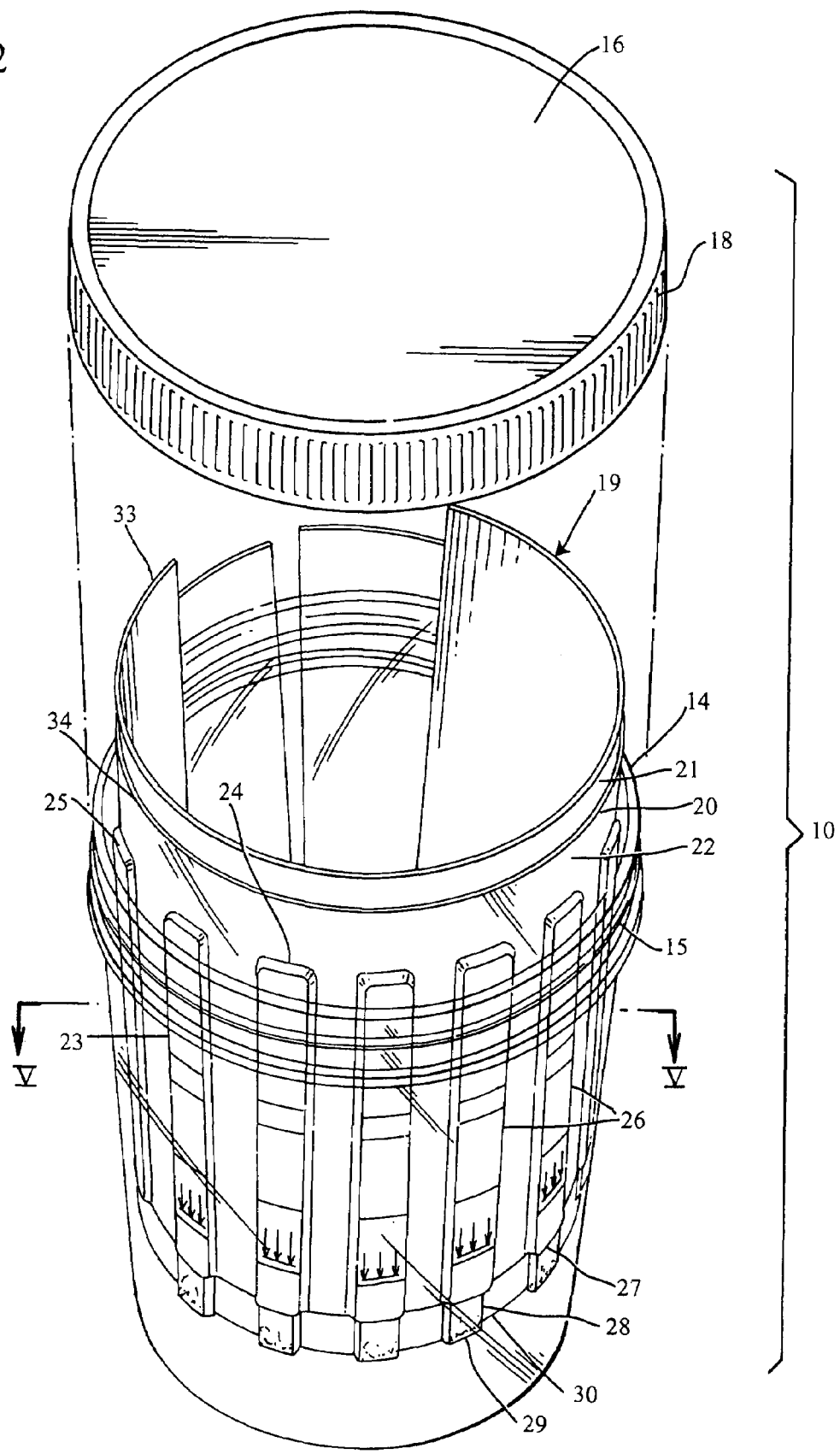
FIG. 2 is a perspective view of the assay device similar to that of FIG. 1 but showing the container cover removed and the assay assembly partially withdrawn from the container.

As may be seen in FIGS. 1 and 2, an assay device is indicated generally at 10 and comprises a cup-like transparent test container 11 having a cylindrical side wall 12, a closed bottom 13 and an open top 14. The cylindrical wall 12 may have a slight taper or be straight.

The open end 14 of the test cup 11 is provided with external threads 15 upon which is seated an outer closure cover or cap 16 provided with corresponding internal threads which are not shown in the drawing. The cover 16 has a circular top surface 17 from the periphery of which depends a cylindrical wall 18 on the inner surface of which there are provided the internal threads.

Positioned within the container 11 is an assay assembly indicated at 19 which is partially shown in FIG. 2 and is completely shown in a flattened position in FIG. 3. The assay assembly comprises a flexible backing member 20 of a plastic material which is preferably liquid impermeable and not reactive with any of the components of fluids which might be tested for drugs of abuse. The backing member 20 may be of an opaque plastic material, for example, white in color, or a transparent plastic material.

The backing member has a front surface 21 upon which is attached a substantially rigid but flexible transparent cover sheet 22 which has molded therein a plurality of parallel elongated pockets 23 each of which is shaped to retain closely therein an immunoassay test strip 24. The pockets 23 are positioned such that they extend longitudinally or vertically within the container when the assay assembly is mounted within the container as seen in FIG. 1. Each pocket 23 has its top 25 and longitudinal sides 26 closed or sealed against the body portion of the cover sheet, but the bottom ends 27 of the pockets are open. The test strips 24 each have bottom portions 28 which extend outwardly of the pockets through these open bottom ends 27 and extreme ends 29 of the bottom portions 28 coincide with a bottom edge 30 of the backing member 20.

The test strips 24 are thus retained in their vertical positions which are axially of the container by being closely enclosed within the pockets 23.

The bottom portion 28 of each test strip functions as a sample receiving area. Each test strip also has a test area 31 and a control area 32.

The test strips 24 may be attached or adhered directly to the front surface 21 of the backing member 20 such that retaining pockets 23 or similar retaining structures are no longer necessary.

The height of the backing member 20 is substantially equal to the inner height of the container such that, when assembled within the container, the bottom edge 30 of the backing member rests on the bottom of the container and a top edge 33 of the backing member is flush with the top edge 14 of the container. Top edge 34 of the cover sheet is spaced downwardly from the top edge 33 of the backing member as may be seen in FIG. 3.

Figure 5:
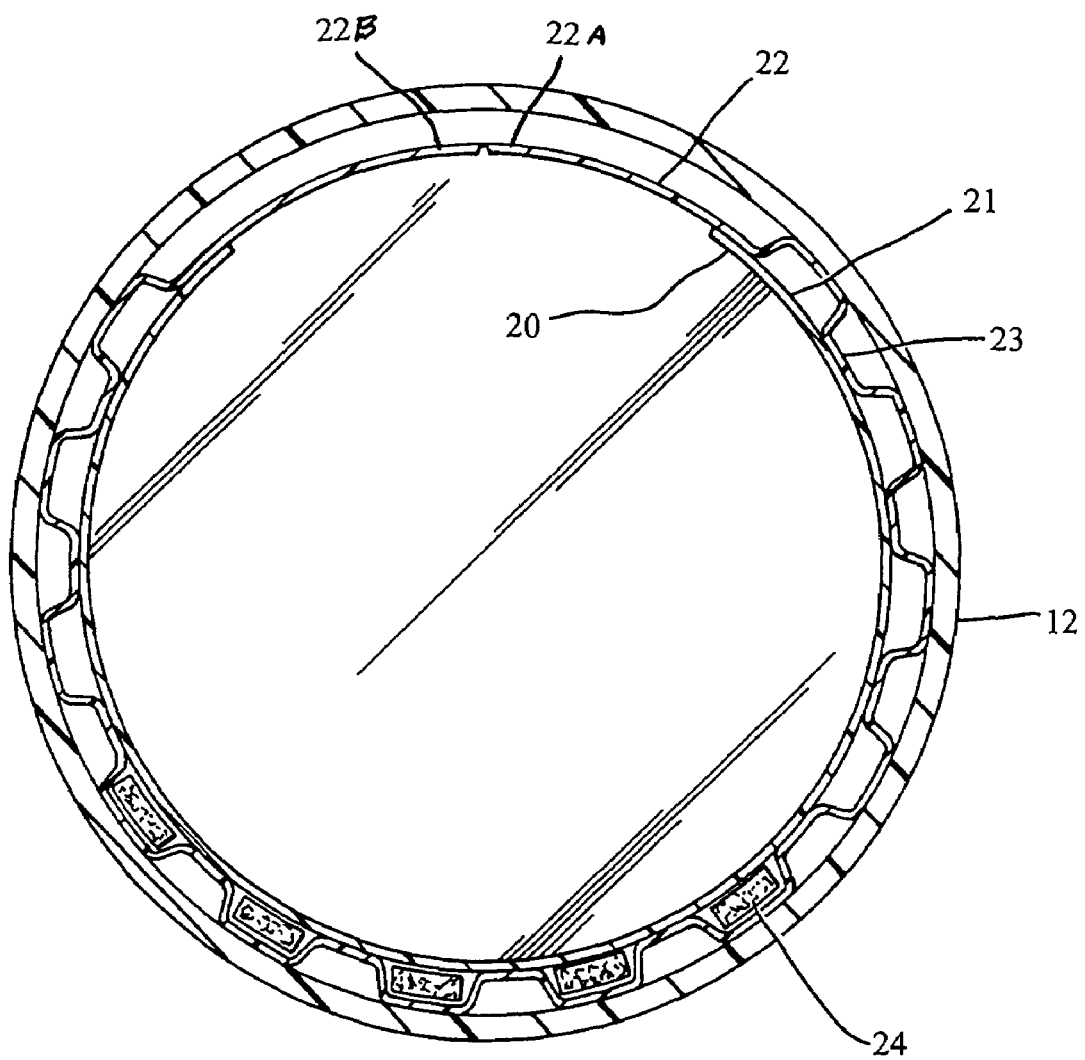
FIG. 5 is a sectional view taken along the line V-V of FIG. 2.

The cover sheet member 22 has a length, when flattened as shown in FIG. 3, which is substantially equal to the inner periphery of the container such that its ends 22A and 22B meet in abutting relation as shown in FIG. 5. However, the length of the cover sheet member may be increased such that the ends 22A and 22B will overlap. These overlapping ends may be provided with a registering depression and protuberance such that they can be snapped together to maintain the cover sheet member in a cylindrical shape which fits closely within the container. Other forms of snaps or clips can be provided to lock abutting or overlapping ends into position.

These particular test strips 24 indicate the presence or absence of the following specific drugs of abuse: PCP, cocaine, amphetamines (AMP), marijuana (THC) and opiates. Test strips 24 may be of the type as made by Phamatech of San Diego, Calif. and Arista Biological of Bethlehem, Pa. Such test strips are characterized as immunoassay assay strips and employ colloidal gold chemistry.

In addition to immunoassay test strips 24 in the pockets 23, a test strip similar in size and shape to the test strips 24 but having adulterant detection means may be placed in a pocket 23. Such an adulterant strip is capable of determining whether a sample of urine has been tampered with by administering either chemical analysis to ensure that the chemical composition of the sample is consistent with that of standard, non adulterated human urine and/or temperature analysis to ensure that the sample has been recently excreted from the donor and has not been brought to the test site by the donor from an earlier excretion. Such adulterant strips are known in the art.

Each of the test strips 24 is a one-step immunoassay in which a specially treated drug, (drug conjugate) competes with a drug which may be present in the sample specimen for the limited number of binding sites on an antibody. The test strip consists of a membrane strip onto which a drug conjugate has been immobilized. A Colloidal gold-antibody complex is dried at one end of the membrane. In the absence of any drug in the urine sample, the colloidal gold-antibody complex moves with the urine sample by capillary action to contact the immobilized drug conjugate. An antibody-antigen reaction occurs forming a visible line in the test area 31 of the test strip. The formation of a visible line occurs when the test is negative for the drug. When a drug is present in the urine sample, the drug or its metabolite will compete with the immobilized drug congate in the test area for the limited antibody sites on the colloidal gold-labeled antibody complex. If a sufficient amount of drug is present, it will fail all of the available binding sites, thus preventing attachment of the label antibody to the drug congate. An absence of a color line or band in the test area is indicative of a positive result. A control zone 32 or line comprised of a different antibody/antigen reaction is present on the membrane strip. The control line is not influenced by the presence or absence of drug in the urine and therefore should be present in all reactions.

In summary, if a single band appears in the control zone 32, then the results are "positive" which indicates that that particular drug is present above a predetermined level which is usually around 50 ng/ml. If two color bands appear, one in the control region and the other in the test region, then the rest of the results are "negative" which indicates that the level of that particular drug is below the predetermined detection of sensitivity.

In the event there are no distinct color bands visible in both the test zone and the control zone or if there is a visible band in the test zone but not in the control zone, then the result is invalid and testing of the specimen is recommended with another test card.

The quantity of liquid sample should be below a "maximum" line 36 which is shown on the container. If the quantity of the sample is above "maximum", the test will not be affected since only a sufficient amount of liquid to conduct the test will flow into the open bottom end of a pocket. This quantity of liquid is limited by the air pressure built up in the closed pocket. The liquid sample contacting the bottom end of each test strip will wick up the test strip by capillary action to reach the chemical agents contained within the test strip to give positive, negative or inconclusive test results. Any excess sample liquid may enter the open end of a pocket but only to a limited degree as described above. However this entering would be after the wicking of the sample has already begun when the sample contacted the bottom portions of the test strips resting on the bottom of the container.

These results will be visible in the test area 31 of the strip and can also be seen through the transparent wall of the container. Thus, this assay device enables one to obtain rapidly a visual, qualitative result which is very advantageous for forensic purposes but is not limited to such purposes.

Thus, it can be seen that the present invention discloses a novel and improved assay device for testing of liquid samples for drugs of abuse. This assay device could be modified to test for other substances by utilizing other agents and chemicals on the test strips. This assay device has a simplified but reliable structure which integrates the assay or test elements within the container in which the liquid sample to be tested is collected. This assay device does not require any pipetting of the liquid sample or specimen, adding or mixing of reagents or other manipulation of the device by the user. This device is particularly suitable for the immediate, point of collection screening for drugs of abuse and offers health care, law enforcement, government, industrial safety and educational professionals a self-contained, one-step screening device capable of identifying illicit drug use within minutes.

It will be understood that this invention is susceptible to modification in order to adapt it to different usages and conditions, and accordingly, it is desired to comprehend such modifications within this invention as may fall within the scope of the appended claims.

What is claimed is:

1. An assay device for testing of liquid samples for drugs of abuse comprising:
   a transparent container for retaining a liquid sample to be tested,
   a backing member within said container and having a front surface visible through said container,
   one or more immunoassay test strips on said front surface of the backing member,
   and means on said backing member for retaining said test strips thereon such that a bottom portion of each strip is exposed to contact a liquid sample which flows upwardly into a said test strip,
   said retaining means also having portions through which at least test portions of said strips are viewable,
   said backing member comprises a thin flexible sheet conforming to the inner surface of said container, said retaining means has a length greater than that of said backing member.

2. An assay device for testing of liquid samples for drugs of abuse comprising:
   a transparent container for retaining a liquid sample to be tested,
   a backing member within said container and having a front surface visible through said container,
   one or more immunoassay test strips on said front surface of the backing member,
   and means on said backing member for retaining said test strips thereon such that a bottom portion of each strip is exposed to contact a liquid sample which flows upwardly into a said test strip,
   said retaining means also having portions through which at least test portions of said strips are viewable,
   said retaining means comprises a sheet member on the front surface of said backing member,
   said sheet member has a length substantially equal to the inner periphery of the container so as to position said test strips closely adjacent to the container wall.

3. An assay device as claimed in claim 2 and further comprising means on the adjoining ends of said sheet member to detachably secure said ends together in a cylindrical shape which can be accommodated within the container.

* * * * *